US00PP16416P2

(12) United States Plant Patent
Dekker

(10) Patent No.: US PP16,416 P2
(45) Date of Patent: Apr. 4, 2006

(54) *CHRYSANTHEMUM* PLANT NAMED 'DEKSPITS'

(50) Latin Name: *Chrysanthemum×morifolium*
Varietal Denomination: Dekspits

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 63 days.

(21) Appl. No.: 11/022,031

(22) Filed: Dec. 24, 2004

(51) Int. Cl.
*A01H 5/00* (2006.01)

(52) U.S. Cl. ..... Plt./288

(58) Field of Classification Search ..... Plt./288
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Dekspits', characterized by its large decorative spider-type inflorescences with quilled-shaped, yellow green to pale yellow-colored ray florets; strong and upright flowering stems; early and uniform flowering response; and good postproduction longevity.

1 Drawing Sheet

Botanical designation: *Chrysanthemum×morifolium.*
Cultivar denomination: 'Dekspits'.

BACKGROUND OF THE INVENTION

The present invention relates to a new and distinct cultivar of *Chrysanthemum* plant, botanically known as *Chrysanthemum×morifolium* and referred to by the name 'Dekspits'.

The new *Chrysanthemum* is the product of a planned breeding program conducted by the Inventor in Hensbroek, The Netherlands. The objective of the breeding program is to create new cut *Chrysanthemum* cultivars with interesting inflorescence forms and attractive floret coloration.

The new *Chrysanthemum* originated from a cross-pollination made by the Inventor on Feb. 25, 2002, in Hensbroek, The Netherlands, of a proprietary selection of *Chrysanthemum* identified as code number 5000,97, not patented, as the female, or seed, parent with a proprietary *Chrysanthemum* selection identified as code number 5003, 60, not patented, as the male, or pollen, parent. The new *Chrysanthemum* was discovered and selected by the Inventor as a single plant within the progeny of the stated cross-pollination in a controlled environment in Hensbroek, The Netherlands.

Asexual reproduction of the new *Chrysanthemum* by terminal cuttings in Hensbroek, The Netherlands since January, 2003, has shown that the unique features of this new *Chrysanthemum* are stable and reproduced true to type in successive generations.

BRIEF SUMMARY OF THE INVENTION

The cultivar Dekspits has not been observed under all possible environmental conditions. The phenotype may vary somewhat with variations in environment such as temperature, day length and light intensity, without, however, any variance in genotype.

The following traits have been repeatedly observed and are determined to be the unique characteristics of 'Dekspits'.

These characteristics in combination distinguish 'Dekspits' as a new and distinct cutlivar:

1. Large decorative spider-type inflorescences with quilled-shaped, yellow green to pale yellow-colored ray florets; typically grown as a single stem-type.
2. Strong and upright flowering stems.
3. Early and uniform flowering response.
4. Good postproduction longevity.

Plants of the new *Chrysanthemum* can be compared to plants of the female parent selection. In side-by-side comparisons conducted in Hensbroek, The Netherlands, plants of the new *Chrysanthemum* differed from plants of the female parent selection in the following characteristics:

1. Plants of the new *Chrysanthemum* were more vigorous than plants of the female parent selection.
2. Plants of the new *Chrysanthemum* flowered earlier than plants of the female parent selection.
3. Color of developing ray florets of plants of the new *Chrysanthemum* was lighter green than color of developing ray florets of the female parent selection.

Plants of the new *Chrysanthemum* can be compared to plants of the male parent selection. In side-by-side comparisons conducted in Hensbroek, The Netherlands, plants of the new *Chrysanthemum* differed from plants of the male parent selection in the following characteristics:

1. Plants of the new *Chrysanthemum* flowered earlier than plants of the male parent selection.
2. Plants of the new *Chrysanthemum* had smaller ray florets than plants of the male parent selection.
3. Plants of the new *Chrysanthemum* and the male parent selection differed in ray floret coloration as plants of the male parent selection had white-colored ray florets.

Plants of the new *Chrysanthemum* can be compared to plants of the *Chrysanthemum* cultivar Anastasia Yellow, disclosed in U.S. Plant Pat. No. 14,293. In side-by-side comparisons conducted in Hensbroek, The Netherlands, plants of the new *Chrysanthemum* differed primarily from plants of the cultivar Anastasia Yellow in the following characteristics:

1. Plants of the new *Chrysanthemum* were more vigorous than plants of the cultivar Anastasia Yellow.
2. Plants of the new *Chrysanthemum* had shorter ray florets than plants of the cultivar Anastasia Yellow.
3. Plants of the new *Chrysanthemum* and the cultivar Anastasia Yellow differed in ray floret coloration as plants of the cultivar Anastasia Yellow had yellow-colored ray florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Dekspits'.

The photograph at the bottom left of the sheet comprises a close-up view of upper surface of a typical inflorescence and a typical leaf of 'Dekspits'.

The photograph at the bottom right of the sheet comprises a close-up view of lower surface of a typical inflorescence and a typical leaf of 'Dekspits'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer and autumn in Hensbroek, The Netherelands, under commercial practice in a glass-covered greenhouse. Plants were initially given long day/short night treatments followed by short day/long night treatments to induce flower initiation and developement. During the production of the plants, day temperatures ranged from 17.5 to 30° C., night temperatures ranged from 18.5 to 24° C. and light levels were about five kilolux. Plants were pinched once and were about ten weeks from planting when the photographs and the description were taken.

Botanical classification: *Chrysanthemum×morifolium* cultivar Dekspits.

Commercial classification: Decorative spider-type *Chrysanthemum* typically grown as a single stem-type cut flower.

Parentage:

*Female or seed parent.*—Proprietary selection of *Chrysanthemum×morifolium* identified as code number 5000,97, not patented.

*Male or pollen parent.*—Proprietary selection of *Chrysanthemum×morifolium* identified as code number 5003,60, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative spider-type cut *Chrysanthemum*; typically grown as a single stem-type; erect and strong flowering stems. Moderately vigorous.

*Flowering stem description.*—Length: About 70 to 80 cm. Diameter: About 6 to 7 mm. Strength: Strong. Texture: Pubescent. Aspect: Erect. Branching habit: Plants are typically grown as single stems. Color: 146B.

*Foliage description.*—Arrangement: Alternate. Length: About 9 to 11 cm. Width: About 6 to 9 cm. Apex: Cuspidate. Base: Attenuate. Margin: Lacerate. Texture, upper and lower surface: Pubescent; rough. Petiole length: About 3 to 5 cm. Color: Developing foliage, upper surface: Darker than 137A. Developing foliage, lower surface: 147B. Fully expanded foliage, upper surface: Between 137A and 147A. Fully expanded foliage, lower surface: 147B. Venation, upper and lower surfaces: 147C. Petiole, upper and lower surfaces: 147C.

Inflorescence description:

*Appearance.*—Decorative spider-type inflorescence form with quilled-shaped ray florets. Inflorescences borne on terminals above foliage. Disk and ray florets develop acropetally on a capitulum. Inflorescences not fragrant. Typically grown as a single stem-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 7.5 weeks later. Early and uniform flowering response.

*Postproduction longevity.*—Cut inflorescences will maintain good substance and form for about 3.5 weeks.

*Quantity of inflorescences per flowering stem.*—Only one per stem when grown as a single stem-type; if grown as a spray-type, about eight inflorescences per flowering stem.

*Inflorescence size.*—Diameter: About 10 to 14 cm. Depth (height): About 4 to 5 cm.

*Inflorescence buds.*—Height: About 1 to 1.5 cm. Diameter: About 1.2 to 1.5 cm. Shape: Oblate. Color: Close to 138A.

*Ray florets.*—Length: About 6 to 7.5 cm. Width: About 6 to 8 mm. Shape: Quilled. Apex: Emarginate. Base: Fused; tubular. Margin: Entire. Texture, upper and lower surfaces: Smooth, glabrous. Number of ray florets per inflorescence: About 400 in numerous whorls. Color: When opening, upper and lower surfaces: 145B to 145C. Fully opened, upper and lower surfaces: 2D; towards the base, 150D.

*Disc florets.*—No disc florets observed.

*Reproductive organs.*—Androecium: Not observed. Gynoecium: Present on ray florets. Stigma length: About 5 mm. Stigma diameter: About 0.5 mm. Stigma color: Close to 155C.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Dekspits', as illustrated and described.

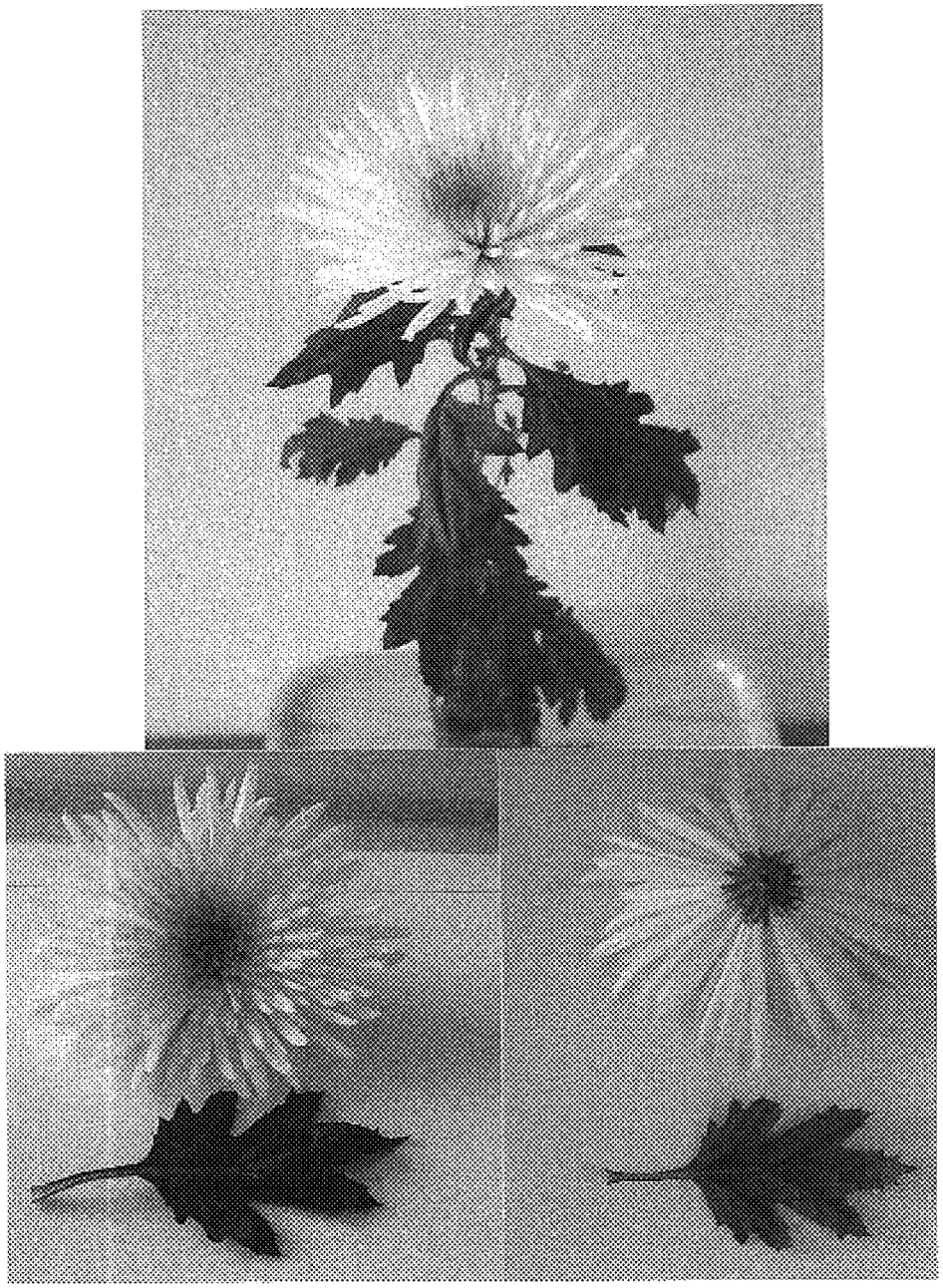

* * * * *